United States Patent
Maritan

(10) Patent No.: US 8,491,530 B2
(45) Date of Patent: Jul. 23, 2013

(54) AUTOINJECTOR WITH TRIGGER POSITIONABLE IN ACTIVE POSITION BY MOVEMENT OF A SAFETY SHIELD AND INDICATION OF THE ACTIVE POSITION

(75) Inventor: Lionel Maritan, Pierre Chatel (FR)

(73) Assignee: Becton Dickinson France, Le Pont de Claix (FR)

( * ) Notice: Subject to any disclaimer, the term of this patent is extended or adjusted under 35 U.S.C. 154(b) by 64 days.

(21) Appl. No.: 12/680,004

(22) PCT Filed: Sep. 25, 2007

(86) PCT No.: PCT/IB2007/003987
§ 371 (c)(1),
(2), (4) Date: Jun. 25, 2010

(87) PCT Pub. No.: WO2009/040605
PCT Pub. Date: Apr. 2, 2009

(65) Prior Publication Data
US 2010/0292653 A1 Nov. 18, 2010

(51) Int. Cl.
*A61M 5/20* (2006.01)

(52) U.S. Cl.
USPC ........... 604/134; 604/110; 604/135; 604/192; 604/154; 604/198; 604/228; 604/67; 604/82; 604/506

(58) Field of Classification Search
USPC ................. 607/110, 134–135, 192, 154, 198, 607/228, 67, 82, 506
See application file for complete search history.

(56) References Cited

U.S. PATENT DOCUMENTS

| | | |
|---|---|---|
| 6,482,186 B1 | 11/2002 | Douglas et al. |
| 2004/0097883 A1 | 5/2004 | Roe |
| 2005/0101919 A1 | 5/2005 | Brunnberg |
| 2005/0203466 A1 | 9/2005 | Hommann et al. |
| 2006/0189938 A1 | 8/2006 | Hommann et al. |
| 2008/0262427 A1* | 10/2008 | Hommann .................... 604/131 |

FOREIGN PATENT DOCUMENTS

| | | |
|---|---|---|
| EP | 0 937 472 B1 | 5/2005 |
| EP | 1 743 666 B1 | 5/2009 |
| WO | 02/47746 A1 | 6/2002 |
| WO | 03/077973 A2 | 9/2003 |
| WO | 2007/036676 A1 | 4/2007 |
| WO | 2007/051330 A1 | 5/2007 |
| WO | 2007056231 A2 | 5/2007 |
| WO | WO 2007/051330 * | 5/2007 |

* cited by examiner

*Primary Examiner* — Theodore Stigell
*Assistant Examiner* — Scott Medway
(74) *Attorney, Agent, or Firm* — Hoffmann & Baron, LLP

(57) ABSTRACT

The invention relates to an automatic injection device (1) for a product contained in a container (50), comprising:
  a housing (8, 19) receiving the container (50), the container being movable between an initial position and an insertion position,
  triggering means (23) for initiating the movement of said container (50) from its initial position to its insertion position, said triggering means (23) being in one of a passive state, in which application of a force on said triggering means does not initiate movement of said container (50), and an active state, in which application of said force on said triggering means does initiate said movement, and
  a safety shield (10) movable with respect to said housing (8, 19) between a first position and a second position, movement of said safety shield (10) from its first position to its second position placing said triggering means (23) in its active state,
characterized in that said device comprises:
  an indicator (19c, 13) that provides an indication to a user of the device (1) that the safety shield (10) has reached its second position.

4 Claims, 8 Drawing Sheets

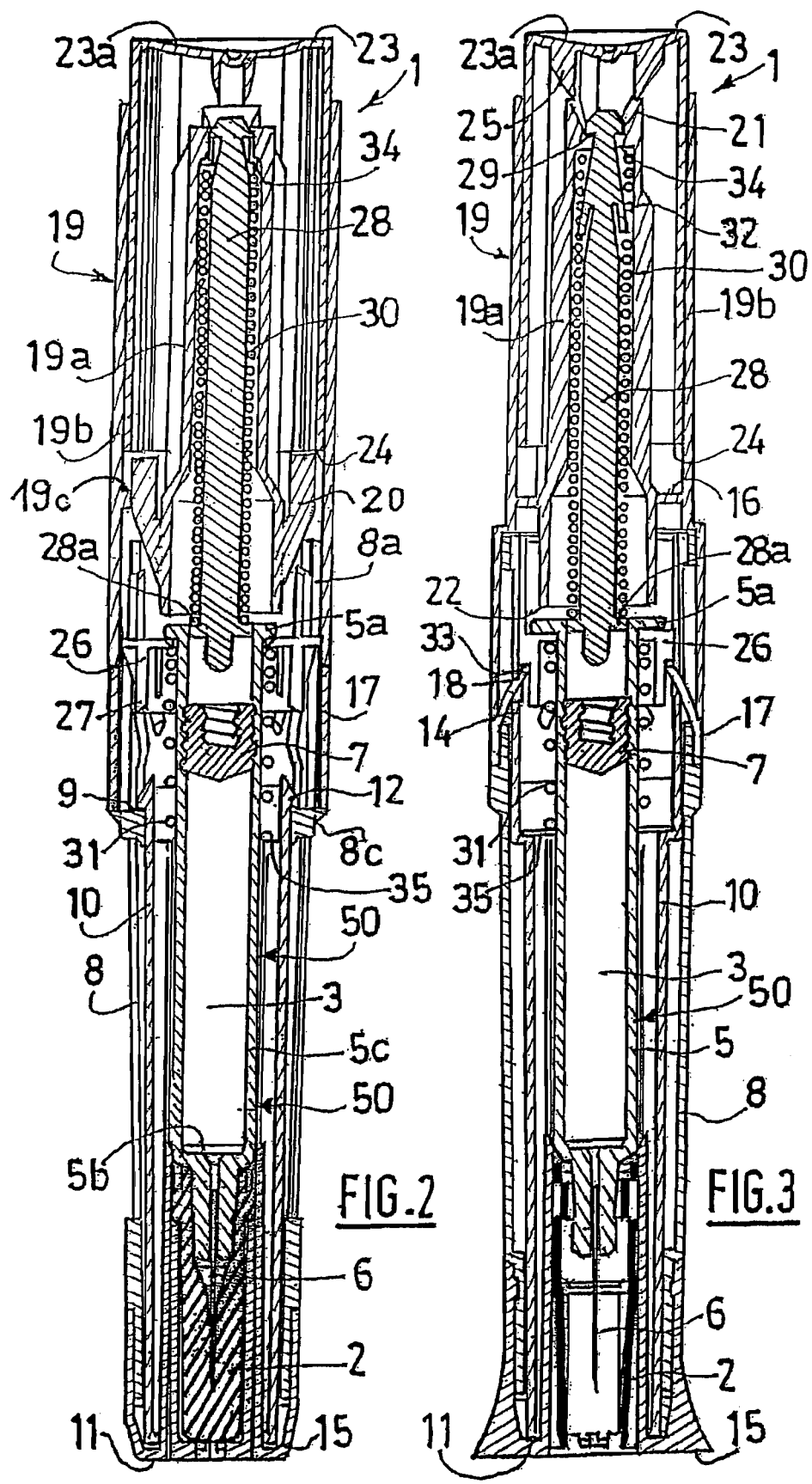

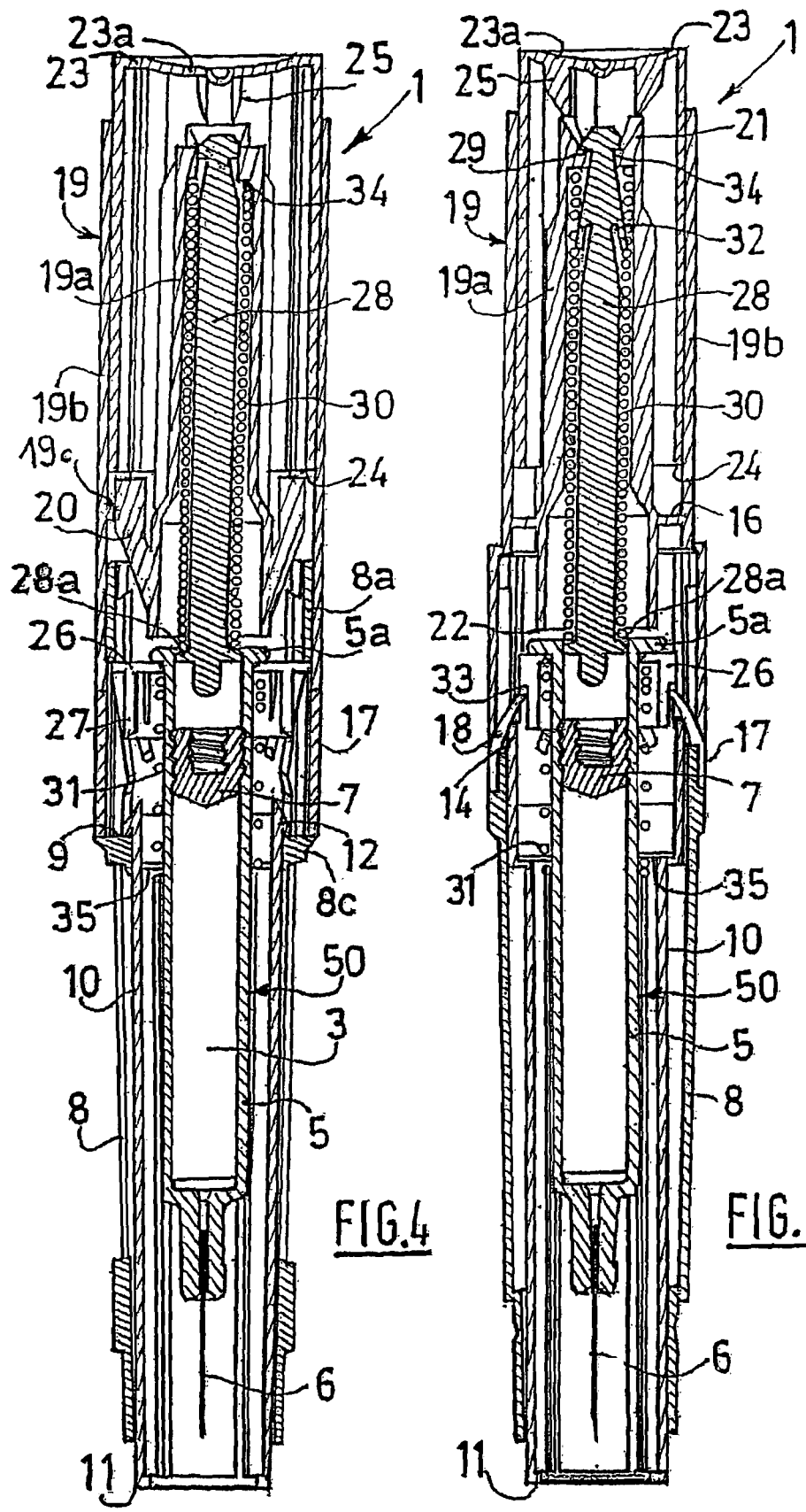

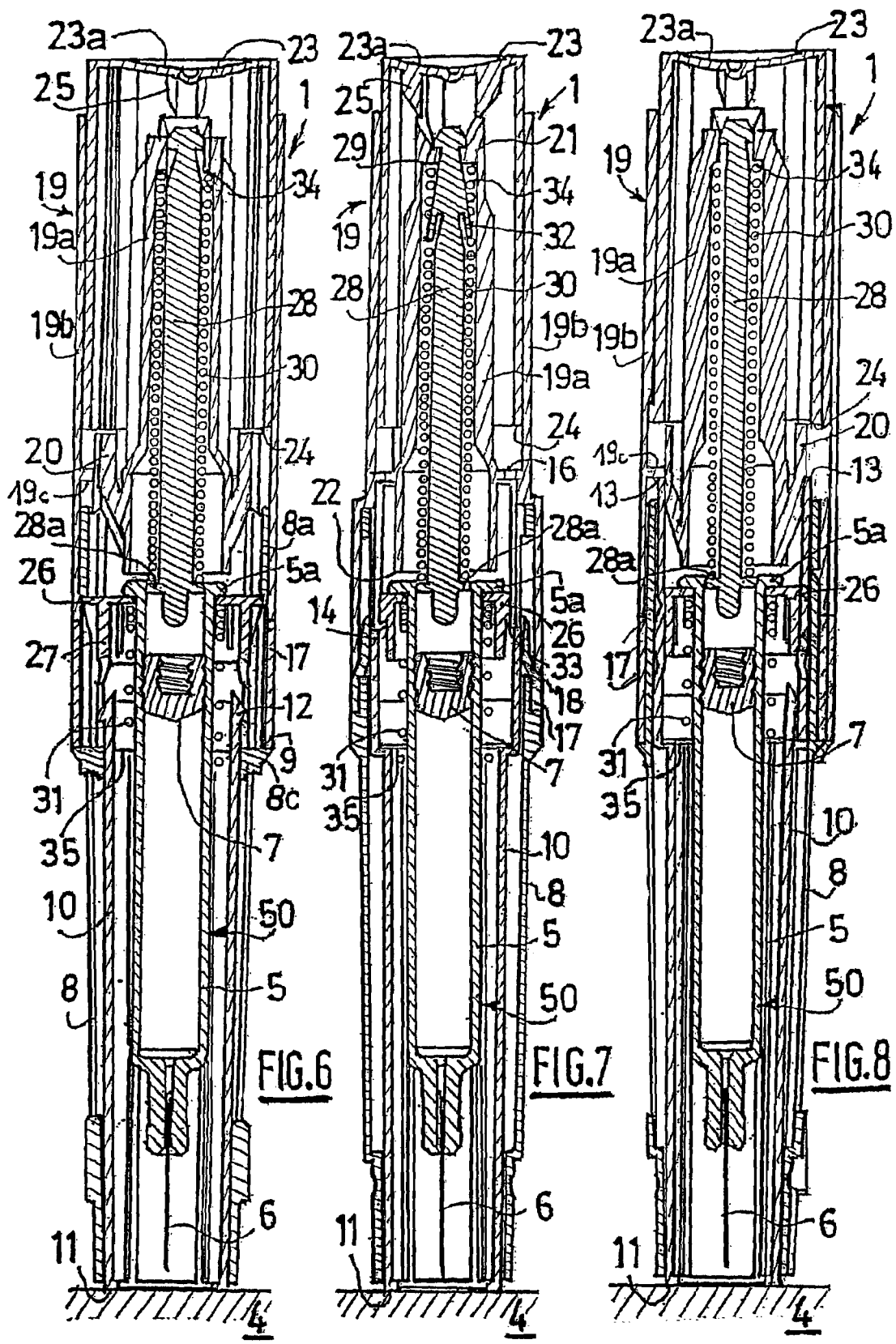

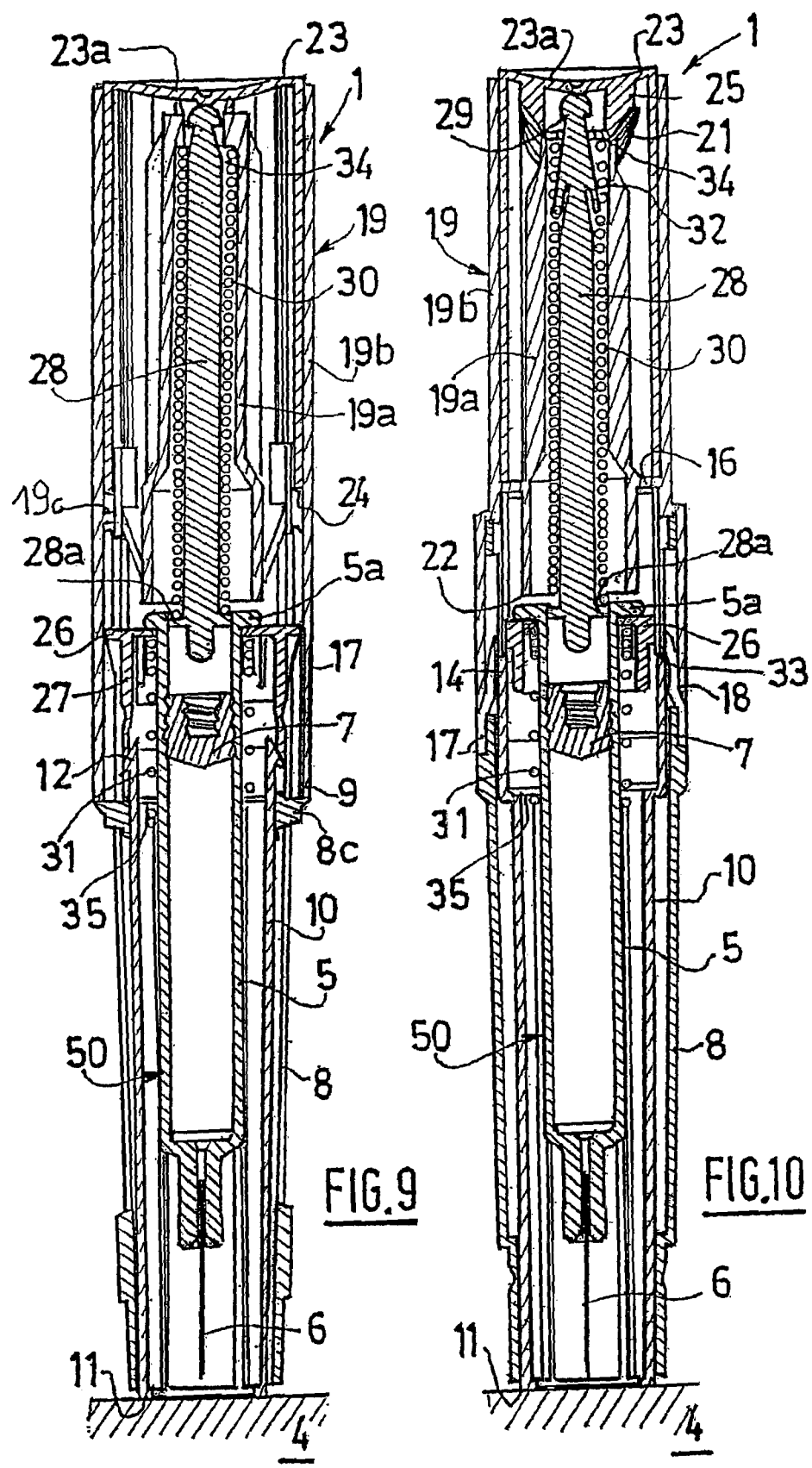

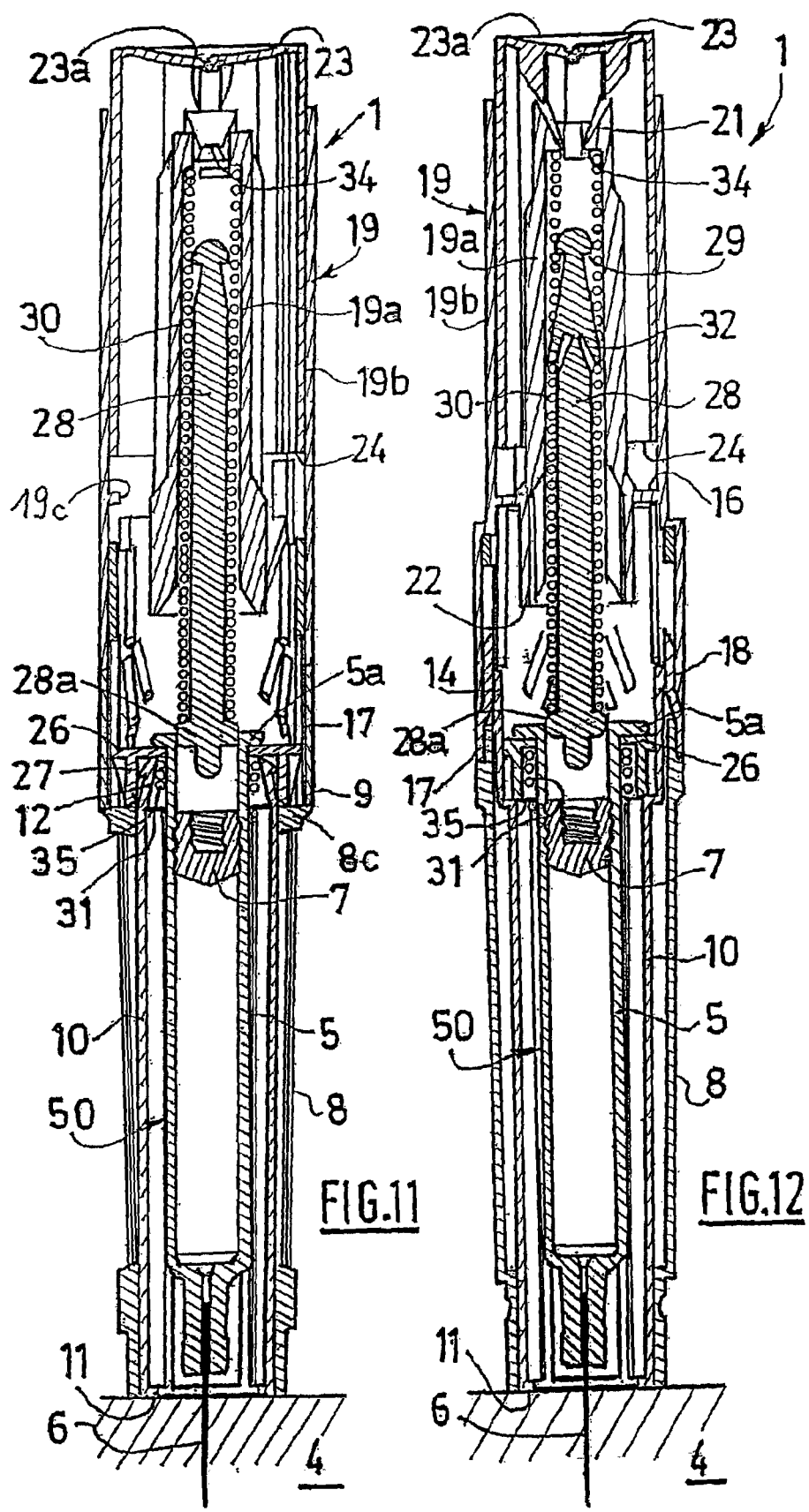

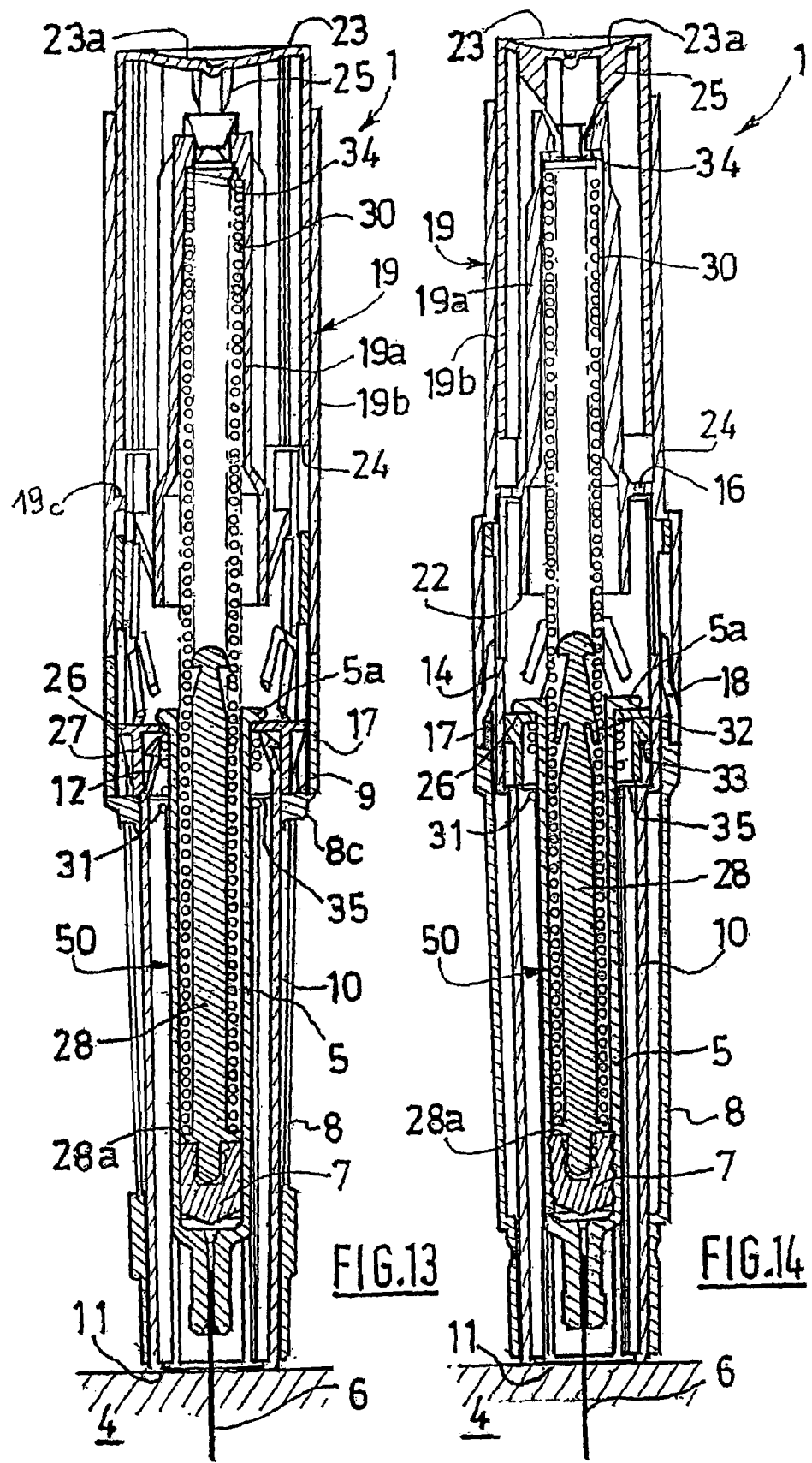

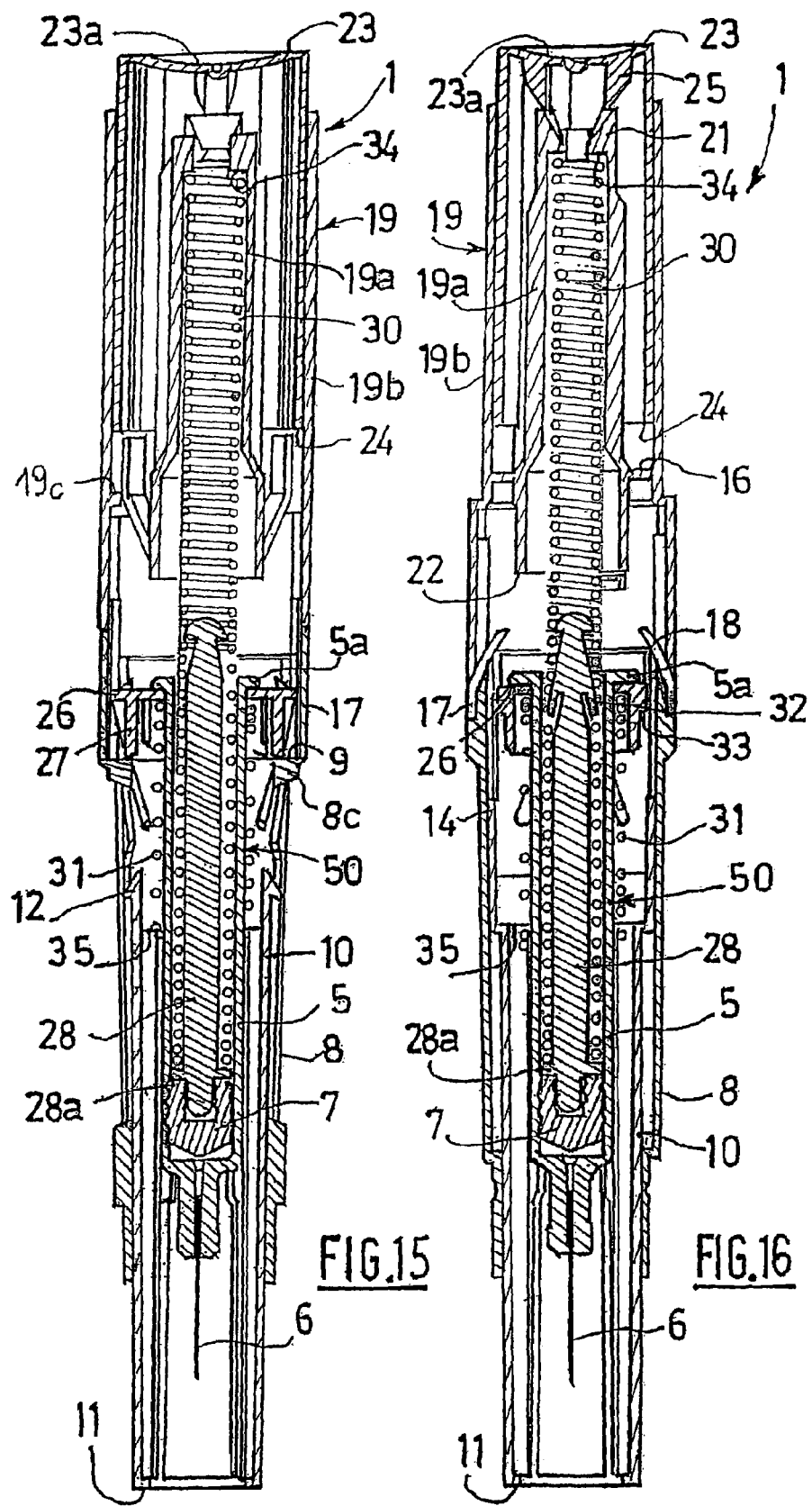

Figure 1:
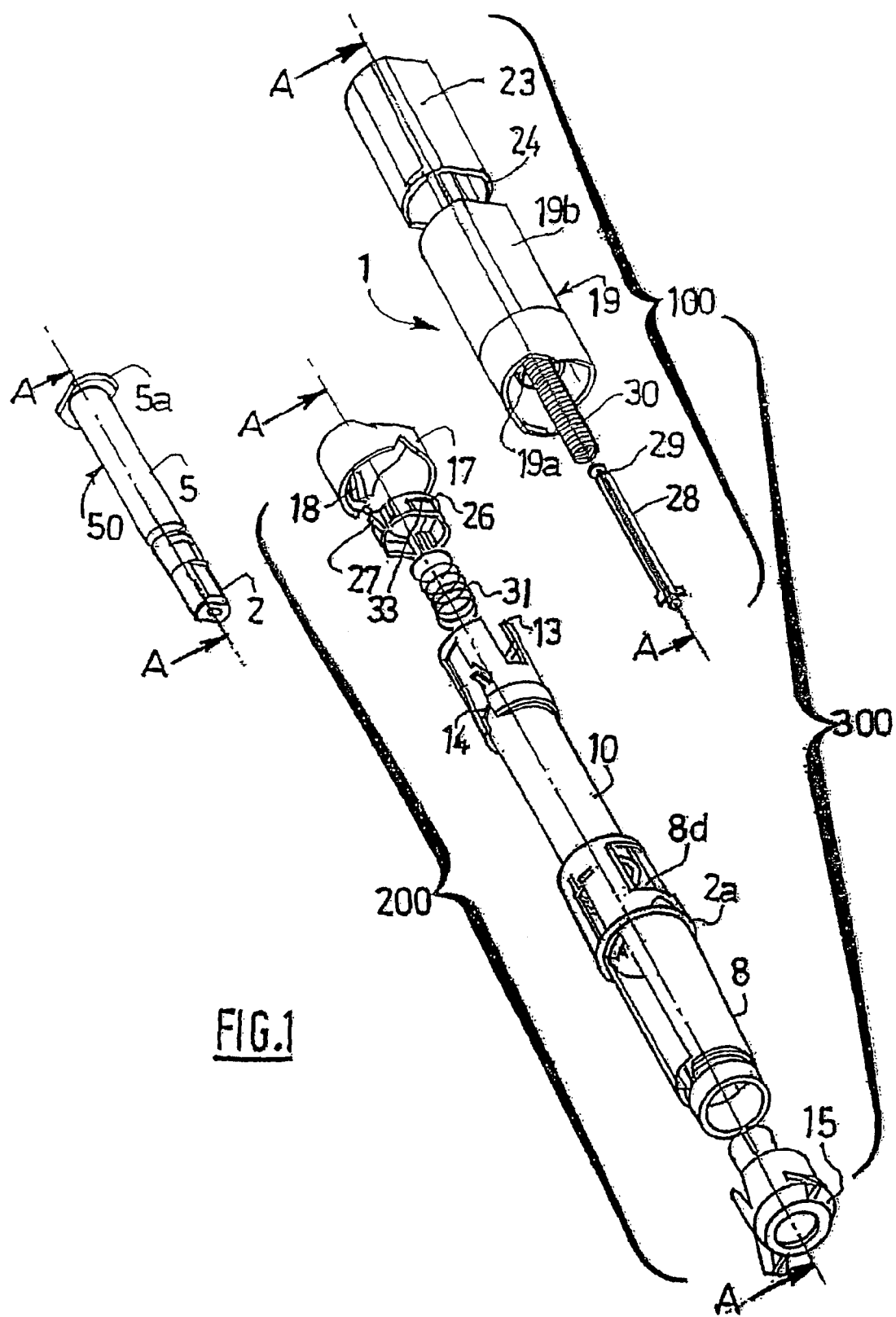

AUTOINJECTOR WITH TRIGGER POSITIONABLE IN ACTIVE POSITION BY MOVEMENT OF A SAFETY SHIELD AND INDICATION OF THE ACTIVE POSITION

The present invention relates to a device for automatic injection of a product in a very safe way, especially for self-injection.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, and the "proximal direction" is to be understood as meaning the opposite direction to the direction of injection.

Some illnesses necessitate regular injections of drugs or products, for instance on a daily basis. In order to simplify the treatment, some self-injectors have been provided in order to allow the patient to perform the injection on its own.

Of course, since the patient is usually neither a nurse nor an educated person in medical devices, such self-injectors must prove to be very simple to use and also very safe. In particular, the insertion of the needle must be performed at the right depth, the correct dose of product must be injected, that is to say a complete injection must be performed, and the injector must be deactivated after use before it is disposed of. Preferably, the needle should not be exposed, before and after use, in order to prevent any accidental needlestick injury.

Another important requirement of these self-injection devices is that they must not be able to be activated inadvertently, before the patient is ready to perform the injection, and in particular before the device is correctly applied at the right injection site.

Nevertheless, it may prove difficult for the end-user to determine whether the self-injection device is correctly positioned at the injection site or not. In particular, when the insertion of the needle and the injection may be activated only after the distal end of the device is applied on the skin and after an outer housing of said device has been pushed towards the injection site, it may be difficult to determine whether such outer housing has been sufficiently pushed towards the skin, in particular because the skin may be more or less tensed at the site of injection and because applying such a distal force on the device may be painful for the patient who may then have not a correct feeling of the device on his skin.

In consequence, there is a need for self-injection devices that would be easy to handle and to operate and for which determination of whether the device is correctly applied or not on the skin would be simple.

The present invention meets this need by proposing a device for automatic injection of a product into an injection site, said device comprising controlling means allowing the end-user to know when the device is correctly applied on the injection site, in particular when a sufficient distal force has been applied on the device so that the insertion of the needle may be activated without any risk of misuse.

The present invention relates to a device for automatic injection of a product into an injection site, said device comprising:

a housing capable of receiving a container movable relative to said housing between an initial position, in which a tip of a needle provided on the container does not extend beyond a distal end of said housing, to an insertion position, distally spaced relative to said initial position and in which the tip of the needle extends beyond said distal end of said housing, triggering means for initiating the movement of the container from its initial position to its insertion position, said triggering means being in one of a passive state, in which application of a force on said triggering means does not initiate said movement of the container, and an active state, in which application of said force does initiate said movement, and a safety shield coupled to and movable with respect to said housing between a first position and a second position proximally spaced with respect to said first position, said safety shield having a free end that is distally spaced beyond a distal end of the needle when said safety shield is in said second position, movement of said safety shield from its first position to its second position placing said triggering means in its active state, characterized in that said device comprises:

an indicator that provides an indication to a user of the device that the safety shield has reached its second position.

The device of the invention allows the end user to know when the outer housing has been pushed towards the injection site with a sufficient force so as to allow to safely triggering the insertion of the needle and thereafter the injection of the product.

Thanks to the device of the invention, the end user does not have to guess when the device is correctly positioned on the skin. In particular, depending on the location of the injection site on the body of a patient, the skin may be more or less tensed. Moreover, the device must be applied on the skin with relatively high force on the skin. Therefore, it is difficult for a patient to have a good feeling or sensation of the position of the device on the skin. The device of the invention allows preventing the misuse of the device. For example, the device of the invention avoids that the insertion of the needle be triggered before the device is correctly positioned on the skin: this is in particular very important so that the insertion depth of the needle be correct and that the injection of the product be completed at the right insertion depth.

In an embodiment of the invention, said indicator is formed by the cooperation of a first element located on said housing and of a second element located on said safety shield, said first and second elements cooperating together when said safety shield reaches its second position, so as to produce said indication.

In an embodiment of the invention, said first element comprises at least a rib located on the inner wall of said housing and said second element comprises at least a tooth located at the proximal end of said safety shield, said tooth coming in contact with said rib and therefore producing a sound when said safety shield reaches its second position.

In an embodiment of the invention, said first element comprises a window located in the wall of said housing and said second element comprises a radial stop located on the outer wall of said safety shield, said radial stop engaging said window and therefore producing a vibration when said safety shield reaches its second position.

In an embodiment of the invention, said device further comprises:

first biasing means coupled to said housing for biasing the container toward said insertion position, said first biasing means being in one of a compressed state, in which the container is in its initial position, and an extended condition, in which the container is in its insertion position, and first retaining means in said housing and arranged to maintain said first biasing means in its compressed condition.

In an embodiment of the invention, said first triggering means is a push button having a distal end, and in that said device further comprises:

second retaining means, arranged to maintain said push button in its passive state, said second retaining means comprising a radially flexible leg provided on an outer sleeve partially receiving said distal end of said push button, said outer sleeve being coupled to said housing, said distal end of said push button being blocked in axial and distal translation by said radially flexible leg, when said safety shield is in its first position, said safety shield further comprising a tooth that engages said second retaining means when said safety shield reaches its second position so as to deflect said radially flexible leg and enable passage of said push button from its passive state to its active state.

In an embodiment of the invention, said first biasing means comprise at least a spring.

The device of the invention will now be further described in reference to the following description and attached drawings in which:

FIG. 1 is an exploded perspective view of an embodiment of the device of the invention, FIG. 2 is a longitudinal cross section view of the device of FIG. 1, before use, with a needle shield and a deshielder, according to a longitudinal plane comprising the longitudinal axis AA' of the device 1, and passing through the middle of window 8d, FIG. 3 is a longitudinal cross section view, shifted of 90° compared to FIG. 1, FIGS. 4 and 5 are longitudinal cross section views of the device of FIG. 1, respectively corresponding to FIGS. 2 and 3, in the initial position, after removal of the needle shield and the deshielder, FIGS. 6 to 8 are longitudinal cross section views of the device of FIG. 1 with the device placed against a user's skin at an injection site, wherein FIG. 8 corresponds to a longitudinal cross section view shifted of 45° compared to FIG. 6, FIGS. 9 and 10 are longitudinal cross section views of the device of FIG. 1 showing the activation of the triggering means, FIGS. 11 and 12 are longitudinal cross section views of the device of FIG. 1 with the container in its insertion position before injection, FIGS. 13 and 14 are longitudinal cross section views of the device of FIG. 1 at the end of the injection step, FIGS. 15 and 16 are longitudinal cross section views of the device of FIG. 1 with the safety shield in the extended position, after removal of the device from the injection site, Referring now to the drawings, the present invention will now be described in detail. FIG. 1 shows an exploded perspective view of a device for automatic injection according to an embodiment of the present invention and generally designated by reference number 1. The inventive device 1 comprises a housing 300 comprised of an upper housing assembly 100 and a lower housing assembly 200 that may be connected to each other by means of a snap-fit connection, screw-type connection, bayonet connection, or other means of connecting two parts together, in an unreleasable way or not. When the device of the injection is of a single use type, the means for connecting the upper housing assembly 100 to the lower housing assembly 200 are made unreachable to the user. A container 50 such as, for example, a syringe, is received in at least one of the upper and lower housing assemblies 100, 200. Preferably, the container 50 is partially received in each of the upper and lower housing assemblies 100, 200, as discussed in more detail herein. The container 50 has a flange 5a defined at an open proximal end, and an injection needle 6 (see, e.g., FIG. 2) at a substantially closed distal end 5b. Lateral walls 5 extend between the proximal and distal ends and define a reservoir 5c sized and shaped to contain a predetermined amount of a product 3 for injection. The injection needle 6 may be fixed to the distal end 5b, or removable therefrom, as a matter of design choice. The injection needle 6 is in fluid communication with the reservoir 5c and provides an outlet port of the container 50 for the product 3. A needle shield 2 is provided at the distal end of the container 50 to cover and protect the needle 6 before use of the device 1. The needle shield 2 also provides for a sealing means of the distal end of the container 50 before use. A piston 7 is provided in the container 50 and which is movable within the reservoir 5c. Movement of the piston 7 causes the product 3 to be expelled from said container 50 through the injection needle 6 during the injection of the product 3 into the patient.

With reference to FIGS. 1-3, the upper housing assembly 100 of the device 1 of the present invention will now be described in further detail. The upper housing assembly 100 has a generally cylindrically shaped outer sleeve 19 comprised of an inner cylinder 19a and an outer cylinder 19b, the cylinders 19a and 19b being linked to each other by at least a radial wall 16. The distal part of the inner cylinder 19a is provided on its outer wall with at least two flexible legs 20 protruding in the proximal direction and being capable of being radially deflected. The proximal end of the inner cylinder 19a is provided with two flexible teeth 21, capable of being radially deflected, and with an inner radial rim 34.

The outer cylinder 19b is provided on its inner wall with a rib 19v. The rib 19c may run on at least a part of the circumference of the inner wall of the outer cylinder 19b The upper housing assembly 100 further comprises a push button 23 received in the outer sleeve 19. The proximal end of the push button 23 is closed by a transversal wall 23a which forms a pushing surface for the user to exert a manual pressure on said push button 23. The distal end 24 of the push button 23 is open. The distal face of the transversal wall 23a is provided with two distal teeth 25.

A plunger rod 28 for causing said piston 7 to move with respect to said container 50, as will be explained later, is received within the inner cylinder 19a of said outer sleeve 19 of the upper housing assembly 100. The plunger rod 28 is provided at its distal end with a flange 28a and at its proximal end with a radial stop 29. The plunger rod 28 is provided, in its proximal portion, with two radial projections 32, the function of which will be explained later.

A first spring 30 is provided between said plunger rod 28 and said inner cylinder 19a: The distal end of the spring 30 bears on the flange 28a of the plunger rod 28, and the proximal end of the spring 30 bears on the distal face of the inner radial rim 34 of the inner cylinder 19a. Spring 30 causes displacement of the container 50 within at least one of the upper and lower housing assemblies 100, 200 from an initial position to an injection position, and further causes movement of the piston 7 within the container 50 to cause the product 3 to be expelled therefrom through the injection needle 6.

With continued reference to FIGS. 1-3, the lower housing assembly 200 of the device 1 of the present invention will now be described in further detail. The lower housing assembly 200 comprises a housing 8 which receives, at least partially the container 50. As will appear later, the container 50 is movable relative to said housing 8 between an initial position, in which a tip of the needle 6 does not extend beyond a distal end of the housing 8 (see, e.g., FIG. 4), and an insertion position, distally spaced relative to said initial position and in which the tip of the needle 6 extends beyond the distal end of the housing 8 and is exposed over a predetermined length (see, e.g., FIG. 11).

The housing 8 has a general cylindrical shape and is open at both ends. The housing 8 has a distal part 8b and a proximal part 8a, the diameter of the proximal part 8a being greater than the diameter of the distal part 8b. The proximal part 8a and the distal part 8b of the housing 8 are joined by a radial wall 8c. The proximal surface 9 of the radial wall 8c forms an abutment surface, the function of which will be explained later. The housing 8 comprises two opposite windows 8d in its proximal part 8a.

The lower housing assembly 200 also includes a safety shield 10 that is at least partially received within the housing 8. A proximal part of the safety shield 10 is provided on its outer wall with two opposite flexible tongues 12, capable of being radially deflected. The proximal part of the safety shield 10 is also provided with two opposite first proximal teeth 13 and with two opposite second proximal teeth 14, distally spaced from said first proximal teeth 13. The safety shield 10 is provided, on its inner wall, with a radial rim 35, distally spaced from said flexible tongues 12.

The safety shield 10 is coupled to the housing 8 and is able to move between a first position and a second position in which the tip of the needle does not extend beyond a distal end of the safety shield 10.

The device 1 of the present invention further comprises an inner ring 26 which receives part of the proximal portion of said container 50, the inner diameter of said inner ring 26 being less than the outer diameter of the flange 5a of said container 50 so as to prevent to container 50 from passing completely through the ring 26 when the ring 26 and container 50 are assembled together (see, e.g., FIG. 3). When assembled together, the inner ring 26 and container 50 may move together within the upper and lower housing assemblies 100, 200 as the container 50 is moved from its initial position to its insertion position (discussed in more detail below). The inner ring 26 comprises at least two distal legs 27 and at least two outer radial rims 33, tangentially spaced from said two distal legs 27.

The device 1 of the present invention also comprises an outer ring 17 which receives, at least partially, said inner ring 26. The outer ring 17 is provided on its inner wall with at least two opposite radially flexible tongues 18 that extend in the proximal direction.

A second spring 31 is provided between said container 50 and said inner ring 26. As shown on FIG. 2, the distal end of the second spring 31 bears on the proximal face of the radial rim 35 of the safety shield 10, and the proximal end of said second spring 31 bears on a distal face of said inner ring 26.

The device 1 of the present invention is also provided with a deshielder 15 for removing the needle shield 2. The deshielder 15 is coupled to the needle shield 2. Prior to use of the device 1, a user removes the deshielder 15, which also removes the needle shield 2.

The functioning of the device 1 will now be explained in reference to FIGS. 4-16. Before providing a detailed description of the operation of a device 1 constructed in accordance with the present invention, the following general description of its operation is provided. The inventive device 1 is provided to a user ready-to-use. The container 50 is filled with a predetermined dose of an injectable product 3—preferably a single dose thus providing a one-time use or disposable injection device. Multi-dose or reusable injection devices are also contemplated by, and with the scope and spirit of the present invention. Prior to use, the user removes the deshielder 15 and the needle shield 2, and places the device 1 against his/her skin at an injection site 4. As the device 1 is pressed against the user's skin, the safety shield 10 is caused to move in the proximal direction and into the housing 8. Due to safety features of the inventive device 1, a user gets an indication that the safety shield 10 has moved the proper predetermined distance in the proximal direction, with respect to the housing, so that the user can then activate the device 1 (i.e., cause the container 50 to move from its initial position to its injection position) safely. Indeed, the container 50 is in its passive state as long as the safety shield 10 has not moved out of its first position. With the device 10 pressed against his/her skin (and the safety shield 10 moved out of its first position in the proximal direction), the container 50 adopts its active state, and the user can activate the device 1 and begin an injection by pressing the push button 23. That will cause the container 50 to move from its initial position to its injection position, which also causes the needle 6 to pierce the user's skin. In addition, by pressing the push button 23 once, the inventive device 1 causes the injectable product 3 to automatically be expelled from the container and into the user's skin. Once the injection is complete, the user removes the device 1 from the injection site and the safety shield 10 is caused to automatically extend from the housing 8 (i.e., lower housing assembly 200) to cover the now-contaminated tip of the needle 6. Advantageously, even if the user removes the device 1 from the injection site 4 before the injection is complete, the safety shield 10 will automatically extend over the tip of the needle. Once the device 1 is removed from the injection site 4 and the shield 10 is extended over the tip of the needle 6, the shield 10 locks in place and cannot thereafter be moved from its locked position in the proximal direction to expose the tip of the needle 6. The used device 1 is thus rendered safe for handling and disposal.

On FIGS. 4 and 5 is shown the device 1 before use, as provided to the user. As shown on FIG. 3, the container 50 is held in its initial position and the first spring 30 is held in a compressed condition by flexible teeth 21 of the inner cylinder 19a being engaged in the radial stop 29 of the plunger rod 28 and the flexible tongues 18 of the outer ring 17 being engaged in the radial rim 33 of the inner ring 26. The inner ring 26 and thus the container 50 are thereby prevented from moving distally. The inner ring 26 is also prevented from moving proximally by the proximal part 8a of the housing 8.

As shown on FIG. 2, the flexible tongues 12 of the safety shield 10 are engaged on the abutment surface 9 of the housing 8. The first spring 30 is in a pressurized or compressed condition, and the second spring 31 is in non-compressed or extended condition.

The flange 5a of the container bears on the inner ring 26. The container 50 is therefore retained in its initial position by the combined actions of the flexible teeth 21 of the inner cylinder 19a, the radial stop 29 of the plunger rod 28 and the inner ring 26, which act as first retaining means of said container 50 in its initial position.

In this position, the needle 6 is protected by the needle shield 2 which is contained within the deshielder 15. The needle 6 and the needle shield 2 are both received within the safety shield 10.

When the user decides to realize the injection, he/she first removes the deshielder 15: by this operation, he/she also removes the needle shield 2, as shown on FIGS. 4 and 5.

As can be seen from FIGS. 4 and 5, after deshielding, the container 50 is still retained in its initial position, and the needle 6 is still protected by the safety shield 10. On these FIGS. 4 and 5, the container 50 is in its passive state.

In the position shown on FIGS. 2 to 5, the push button 23 is also in a passive state such that depression by a user on the pushing surface 23a will not cause the device 1 to make an injection. Although the push button 23 is movable in the distal direction when the button 23 is in the passive state, it cannot cause activation of the device 1 because a distal end 24 of the push button 23 comes in contact with the proximal end of the flexible legs 20 of the inner cylinder 19a (see FIG. 4). The push button 23 is therefore stopped and the device 1 can not be triggered or activated. The push button 23 and the container 50 are both in their passive state. The device 1 of the invention is therefore particularly safe, as it cannot be triggered through a single action (i.e., only by pressing on the push button 23).

In the example shown on the figures, the triggering of the device 1 of the invention requires at least that the push button 23, which acts as a deactivating means of the first retaining means of the first spring 30 in its compressed condition and of the container 50 in its initial position, be previously caused to pass from a passive state, in which the exercise of a manual pressure by the user on said push button 23 does not cause the release of said first retaining means, to an active state, in which the exercise of said manual pressure does cause the release of said first retaining means. As discussed in more detail below, movement of the safety shield 10 out of its first position causes the push button 23, and in consequence the container 50, to move from their passive state to their active state.

This step is shown on FIGS. 6 and 7. In this step, the user applies the device 1 on the injection site 4 by means of the bearing surface 11 of the safety shield 10. He/she then exerts a distal force on the housing 8 thereby causing the safety shield 10 to move relative to said housing 8 from a first position, namely a rest position, shown on FIGS. 4 and 5, for example, to a second position, namely a bearing position, shown on FIGS. 6 and 7—the second position being proximally spaced relative to said first position. During this movement, the first proximal teeth 13 of the safety shield 10 contact the flexible legs 20 of the inner cylinder 19a and cause the flexible legs 20 to deflect radially towards the center of the device 1, as shown on FIG. 8. Once deflected as just described, the flexible legs 20 do not opposingly face the distal end 24 of the push button 23 and said push button 23 is now in its active state.

Moreover, when the safety shield 10 reaches its second position, the first proximal teeth 13 come in contact with the rib 19c of the housing (see FIG. 8) and this contact provokes a noise. The user therefore gets an audible indication that the safety shield 10 has moved on the necessary predetermined distance for the user to activate the triggering means safely. By hearing this noise, the user gets the indication that the safety shield has reached its second position. The user can then activate the triggering means safely, with the guarantee that the device is correctly applied on the injection site and that the injection may be activated without risk of misuse.

As can be seen from FIGS. 6-8, in its second position, the safety shield 10 has a free end 11 that is distally spaced beyond a distal end of the needle 6.

In the example shown on the figures, movement of the safety shield 10 from its first position to its second position also places the container 50 in its active state. In an alternative embodiment of the invention not shown, the container 50 could be in its active state from the start. With reference to FIG. 7, during such movement of the safety shield 10, the second proximal teeth 14 of the safety shield 10 contact the radially flexible tongues 18 of the outer ring 17 and cause the flexible tongues 18 to deflect radially thereby disengaging them from the radial rim 33 of the inner ring 26, in which they were engaged. Upon such deflection, the container 50 is placed in its active state and able to move to its injection position. However, movement of the container 50 to its injection position does not occur upon the release or deflection of the flexible tongues 18 because the inner ring 26 and container 50 are biased in the proximal direction by the second spring 31. Moreover, the inner ring 26 is also blocked in the proximal direction by the proximal part 8a of said housing 8. As a consequence, during this first step, although the container 50 is able to move in the distal direction, it does not and is retained in its initial position. Actually, the container 50 is retained in its initial position, but now in its active state, so that movement of the container out of its initial position may now be permitted, although only upon pressing of the push button 23.

In an alternative embodiment of the invention, the push button 23 is not coupled to said plunger rod 28 when the push button 23 is in its passive state. The push button 23 is then allowed to move in its passive state but it is prevented to have any action with the plunger rod 28. After application of the device 1 on the injection site 4, the safety shield 10 causes the plunger rod 28 to be coupled to the push button 23 which is then placed in its active state. Like described above, the user may get the indication that the safety shield 10 has reached its second position by means of a tooth located on the safety shield 10 coming in contact with a rib located on the housing.

In an alternative embodiment of the invention, not shown, the user gets a sensitive indication that the safety shield has reached its second position, for example by cooperation of a first element located on the housing and a second element located on the safety shield. For instance, the first element comprises a window located in the wall of the housing and the second element comprises a radial stop located on the outer wall of the safety shield. When the safety shield reaches its second position, the radial stop engages the window and therefore produces a vibration. By feeling this vibration, the user gets the indication that the safety shield has reached its second position. The user can then activate the triggering means safely, with the guarantee that the device is correctly applied on the injection site and that the injection may be activated without risk of misuse.

The push button 23 being now in its active state, the user can, in a second step, trigger the device 1 to start the automatic injection. The activation of the push button 23 is shown on FIGS. 9 and 10. The user exerts a manual pressure on the pushing surface 23a of the push button 23: the push button 23, which is no more stopped by the flexible legs 20, moves distally, thereby causing the distal movement of the teeth 25 of the push button 23. During this movement, the teeth 25 come in contact with the flexible teeth 21 of the inner cylinder 19a and cause said flexible teeth 21 to deflect radially and outwardly, as shown on FIG. 10.

The flexible teeth 21 are now disengaged from the radial stop 29 of the plunger rod 28 and the first spring 30 is now free to move from its compressed condition to an extended condition. The first spring 30 expands and causes the plunger rod 28, which is coupled to said container 50, to move in the distal direction. Because of the previous disengagement of the flexible tongues 18 from the radial rim 33 of the inner ring 26, both the inner ring 26 and the container 50 are now free to move distally, i.e. the container 50 may move to its injection position. The first spring 30 therefore pushes distally the plunger rod 28, the container 50 and the ring 26 as the container is caused to move to its injection position.

Movement of the container 50 to its injection position also causes the needle 6 to pierce the user's skin at the injection site 4. The depth of insertion of the needle 6 into the user' skin at the injection site 4 is controlled by the interaction between the distal legs 27 of said inner ring 26 and the abutment surface 9 of the housing 8, as shown on FIGS. 11 and 12. When the end of distal legs 27 engage abutment surface 9, movement of the container 50 in the distal direction, and thus, injection of the needle 6 into the user's skin, is stopped. The needle 6 is now inserted into the injection site 4 over a predetermined length, said predetermined length being controlled by the engagement of said distal legs 27 on said abutment surface 9, as shown on FIGS. 11 and 12.

In another embodiment of the invention, the insertion depth of the needle 6 could be controlled by the engagement of said distal legs 27 on an abutment surface provided on the safety shield 10. Alternatively, the insertion depth could be variable, and/or controlled. While it may not be desirous to enable a user to vary the injection depth, such control may be desirable in the hands of a pharmaceutical company or supplier of the injection device 1 of the present invention. For example, different injection depths may be desired for different pharmaceutical compounds (i.e., injectable products). Depending upon the product 3 provided in the container 50, it may be necessary for the pharmaceutical company or other supply of the inventive device 1 to set the injection depth for each different compound. This may be accomplished by enabling the pharmaceutical company to control the spatial relationship between the distal legs 27 and abutment surface 9—that relationship controlling the injection depth of the needle 6.

During this insertion of the needle 6, the inner ring 26 has moved distally and its distal legs 27 have come in contact with the flexible tongues 12 of the safety shield 10, causing the flexible tongues 12 to be deflected radially and inwardly, as shown on FIG. 11. During this same distal movement of the inner ring 26, the second spring 31 has been caused to compress and has reached a pressurized or compressed condition, as shown on FIG. 11. Yet, the distal end of said second spring 31 bears on the radial rim 35 of said safety shield 10 which is maintained against the injection site 4 by the distal pressure exerted by the user on the device 1 and said second spring 31 is therefore not free to expand.

It can be seen from FIG. 11 that because of the now deflected state of the flexible tongues 12, the abutment surface 9 no longer be an obstacle to the distal movement of said flexible tongues 12. Therefore, in the insertion position of the needle as shown on FIGS. 11 and 12, removal of the device 1 from the injection site 4 by the user at this stage of the operation would cause the safety shield 10 to be moved distally to an extended position by the second spring 31 to cover and protect the needle 6. When in its extended position, the safety shield 10 is locked against proximal movement thereby preventing unintended access to the contaminated needle 6.

As noted above, once the container 50 is in its insertion position, the safety shield 10 is movable to its extended position. In consequence, in this position, the safety shield 10 automatically extends to its extended position when a user removes the device 1 from the injection site 4 any time after the container 50 has been moved to its injection position. The device 1 of the invention is therefore particularly safe and it prevents accidental needlestick injuries even in case said device 1 is removed from the injection site 4 before the injection of the product is actually completed.

At the end of the insertion step, the force of the first spring 30, which continues its expansion, overcomes the friction of the flange 28a of the plunger rod 28 against the inner wall of the container 50, and the distal end of the plunger rod 28 comes in contact with the piston 7 with which it becomes coupled at least in the distal direction.

The first spring 30 still continues its expansion, overcomes the stiction of the piston 7 and the piston 7 is caused to move distally, realizing the injection of the product 3, as shown on FIGS. 13 and 14. The injection is therefore completed automatically without any manual operation from the user.

When the injection is completed, the user removes the device 1 from the injection site 4, as shown in FIGS. 15 and 16. As noted above, removal of the device 1 from the injection site 4 any time after the container 50 is in its injection position will result in movement of the safety shield 10 to its extended position in which it is locked over the needle 6 (i.e., the tip of the needle 6 does not extend beyond a distal end of the safety shield 10). Movement of the safety shield 10 is effected by the second spring 31 as it returns to an extended condition upon removal of the device 1 from the injection site 4.

Movement of the safety shield 10 out of its extended position is prevented by cooperating structural elements provided on the safety shield 10 and the inner ring 26, for example.

The injection device of the invention allows automatic self injection of a product to be performed by a patient without any risk of misuse. In particular, the device of the invention allows the user to be informed that the device is correctly placed on the skin and that he can trigger the injection without risk. Moreover, the safety shield of the device of the invention is in its active state right at the end of the insertion step, before the injection step actually begins. In this way, even if the patient decides to withdraw the device before the end of the injection, then the safety shield automatically extends over the needle.

The invention claimed is:

1. A device for automatic injection of a product into an injection site, said device comprising:
   a housing capable of receiving a container movable relative to said housing between an initial position, in which a tip of a needle provided on the container does not extend beyond a distal end of said housing, to an insertion position, distally spaced relative to said initial position and in which the tip of the needle extends beyond said distal end of said housing;
   trigger for initiating the movement of the container from its initial position to its insertion position, said trigger being in one of a passive state, in which application of a force on said trigger does not initiate said movement of the container, and an active state, in which application of said force on said trigger does initiate said movement;
   a safety shield coupled to and movable with respect to said housing between a first position and a second position proximally spaced with respect to said first position, said safety shield having a free end that is distally spaced beyond a distal end of the needle when said safety shield is in said second position, movement of said safety shield from its first position to its second position placing said trigger in its active state; and
   an indicator that provides an indication to a user of the device that the safety shield has reached its second position,
   wherein said indicator being formed by the cooperation of a first element located on said housing and of a second element located on said safety shield, said first and second elements cooperating together when said safety shield reaches its second position, so as to produce said indication, and
   wherein said first element comprises at least a rib located on the inner wall of said housing and said second element comprises at least a tooth located at the proximal end of said safety shield, said tooth being unitarily formed with said safety shield so as to move with said safety shield, said tooth coming in contact with said rib and therefore producing a sound when said safety shield reaches its second position.

2. Device according to claim 1, characterized in that said device further comprises:
- first biasing means coupled to said housing for biasing the container toward said insertion position, said first biasing means being in one of a compressed state, in which the container is in its initial position, and an extended condition, in which the container is in its insertion position, and
- first retaining means in said housing and arranged to maintain said first biasing means in its compressed condition.

3. Device according to claim 1, characterized in that said trigger is a push button having a distal end, and in that said device further comprises:
- push button retaining means, arranged to maintain said push button in its passive state, said push button retaining means comprising a radially flexible leg provided on an outer sleeve partially receiving said distal end of said push button, said outer sleeve being coupled to said housing, said distal end of said push button being blocked in axial and distal translation by said radially flexible leg when said safety shield is in its first position,
- wherein said safety shield further comprising a tooth that engages said push button retaining means when said safety shield reaches its second position so as to deflect said radially flexible leg and enable passage of said push button from its passive state to its active state.

4. Device according to claim 2, characterized in that said first biasing means comprise at least a spring.

* * * * *

UNITED STATES PATENT AND TRADEMARK OFFICE
CERTIFICATE OF CORRECTION

PATENT NO.       : 8,491,530 B2
APPLICATION NO.  : 12/680004
DATED            : July 23, 2013
INVENTOR(S)      : Lionel Maritan It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 156 days.

Signed and Sealed this

Eighth Day of September, 2015

Michelle K. Lee
*Director of the United States Patent and Trademark Office*